United States Patent [19]

Ueda et al.

[11] 4,326,881
[45] Apr. 27, 1982

[54] PHENYLPYROL DERIVATIVES

[75] Inventors: Akiyoshi Ueda, Hiratsuka; Hideo Takagi, Kanagawa; Kazuhiko Ohkuma, Ninomiyamachi, all of Japan

[73] Assignee: Nippon Soda Company Limited, Tokyo, Japan

[21] Appl. No.: 970,153

[22] Filed: Dec. 18, 1978

[30] Foreign Application Priority Data

Jan. 31, 1978 [JP] Japan ..................... 53-9752

[51] Int. Cl.³ .................. A01N 43/36; C07D 207/323
[52] U.S. Cl. ..................... 71/95; 260/313.1; 260/326.5 J; 260/326.46
[58] Field of Search ............ 260/313.1, 326.5 J; 71/95; 424/274

[56]  References Cited

U.S. PATENT DOCUMENTS

| 3,428,648 | 2/1969 | Umio et al. | 260/313.1 |
| 3,487,089 | 12/1969 | Umio et al. | 260/313.1 |

FOREIGN PATENT DOCUMENTS

| 45-14064 | 8/1966 | Japan | 260/313.1 |
| 42-6746 | 3/1967 | Japan | 260/313.1 |
| 46-31223 | 6/1967 | Japan | 260/313.1 |
| 47-42833 | 10/1967 | Japan | 260/313.1 |
| 42-25888 | 12/1967 | Japan | 260/313.1 |
| 50-2011 | 1/1975 | Japan | 260/313.1 |
| 51-88630 | 8/1976 | Japan | 260/313.1 |

OTHER PUBLICATIONS

Morrison & Boyd; Organic Chemistry 2nd Edition. p. 751 (1969).

*Primary Examiner*—Mary C. Lee
*Attorney, Agent, or Firm*—George B. Oujevolk

[57]  ABSTRACT

Compounds of the general formula

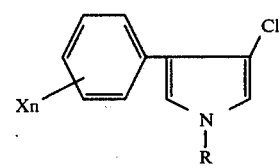

wherein
Xn is 2-Cl, 3-Cl, 2,3-Cl$_2$ or 3-CF$_3$, and
R is hydrogen or acetyl,
with the proviso that Xn is 2,3-Cl$_2$ in the case of R being hydrogen, are outstanding effective fungicides.

1 Claim, No Drawings

PHENYLPYROL DERIVATIVES

DETAILED DESCRIPTION OF THE INVENTION

The present invention relates to a novel phenylpyrol derivatives, to a process for the preparation thereof and their uses as fungicides, in particular to a fungicidally active composition and method for controlling fungi.

It is hitherto known that various 3-phenylpyrols, for example, 3-(2-nitro-3-chlorophenyl)-4-chloropyrol, 1-acetyl-3-(2-nitro-3-chlorophenyl)-4-chloropyrol, 3-(3,4-dichlorophenyl)-4-chloropyrol, have antibiotic activity and are useful as medicines.

It is also known that some 3-phenylpyrols, for example, 3-(2-nitro-3-chlorophenyl)-4-chloropyrol (Japanese Published Unexamined Patent Application No. 88630/1976), 3-(3-trifluoromethylphenyl)-4-chloropyrol (Japanese Published Examined Patent Application No. 2011/1975) are effective for the control of plantpathogin.

The inventors have studied the fungicidal activity of various 3-phenylpyrols and have found that 3-phenylpyrols of the formula

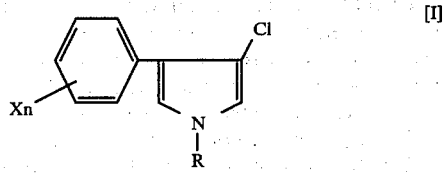

wherein
Xn is 2-Cl, 3-Cl, 2,3-Cl$_2$ or 3-CF$_3$, and
R is hydrogen or acetyl,
with the proviso that Xn is 2,3-Cl$_2$ in the case of R being hydrogen have outstandingly superior fungicidal activity to the known 3-phenylpyrols.

The compounds of the present invention can be prepared by the reaction shown as follows:

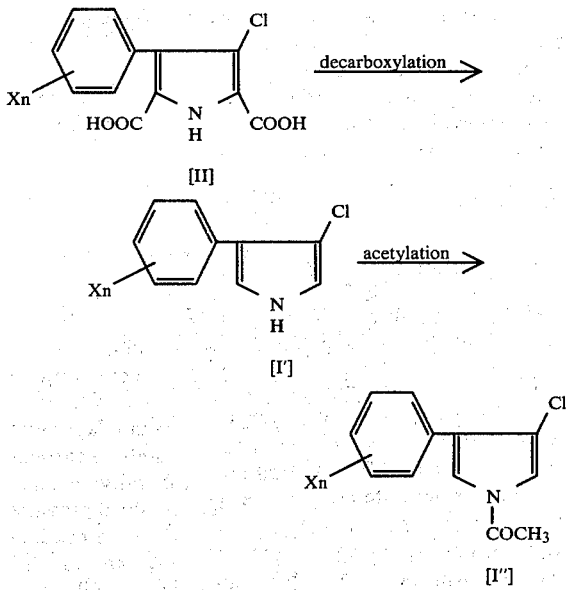

The decarboxylation reaction is carried out by heating the compound of the formula [II] in an inert solvent. As an inert solvent, amines having a boiling point of the applied reaction temperature or above, such as quinoline and dimethyl aniline, may be used. Further, concentrated sulfuric acid may be used as an solvent. The reaction may be performed at a temperature in the range of 100° to 250° C., preferably from 120° to 220° C. in the case of the employed solvent being the amines, and preferably from 100° to 130° C. in the case of the solvent being sulfuric acid. The reaction time is ordinarily from about 20 minutes to several hours, except that it is from 5 to 20 minutes when the solvent is sulfuric acid. A catalyst is preferably used when the solvent is the amines. As the catalyst, cupric oxide or cupric salt such as cupric chloride or cupric sulfate may be used.

The above mentioned acetylation reaction is carried out by reacting the compound of the formula [I'] with acetylimidazole at a temperature of 70° to 150° C., preferably 90° to 120° C. for about one hour. In that case, the reaction may be carried out by fusing the mixture of the compound of the formula [I'] and acetylimidazole, or by heating the compound of the formula [I'] with a catalytic amount of acetylimidazole or imidazole in acetic anhydride.

Further, the acetylation reaction may be carried out by reacting sodium or potassium salt of the compound of the formula [I'] with acetyl halides, or by reacting the compound of the formula [I'] with acetic anhydride in the presence of triethylamine.

The compound of the formula [II] may be prepared by usual methods, for example by the following reaction (in the following equation, Y indicates the group,

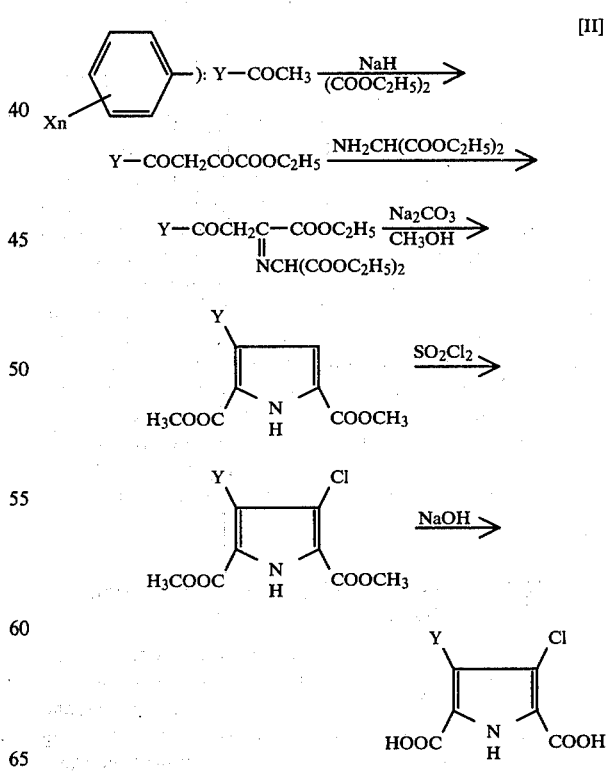

The compounds of the present invention are shown in Table 1.

TABLE 1

| Compound No. | Chemical Structure | Physical Constant |
|---|---|---|
| 1 | 2,3-dichlorophenyl group with Cl-substituted pyrrole, N-H | m.p. 58–59° C. |
| 2 | 2,3-dichlorophenyl group with Cl-substituted pyrrole, N-COCH$_3$ | m.p. 97° C. |
| 3 | 3-CF$_3$-phenyl with Cl-substituted pyrrole, N-COCH$_3$ | m.p. 70–71.5° C. |
| 4 | 2-Cl-phenyl with Cl-substituted pyrrole, N-COCH$_3$ | m.p. 82–84° C. |
| 5 | 3-Cl-phenyl with Cl-substituted pyrrole, N-COCH$_3$ | m.p. 88–90° C. |

The following examples illustrate production of compounds according to the invention:

EXAMPLE 1

Preparation of 4-chloro-3-(2,3-dichlorophenyl)pyrol

(1) Ethyl 4-(2,3-dichlorophenyl)-2,4-dioxobutyrate

To 14 g of sodium hydride (50%) were added dropwise 21.3 g of diethyl oxalate, 0.54 ml of ethanol and then 160 ml of ether solution containing 30 g of 2,3-dichloroacetophenone with stirring under cooling with ice. The reaction was carried out under the state free from water. The reaction was continued at room temperature for 40 minutes with stirring after the dropping and further carried out for 45 minutes under reflux. The reaction mixture was poured into ice-cold water containing 17.5 g of acetic acid and after stirring the mixture was filtered. The organic layer was separated, dehydrated and concentrated. The residue was recrystallized from n-hexane to obtain 14.5 g of ethyl 4-(2,3-dichlorophenyl)-2,4-dioxobutyrate (white needles, m.p. 57°–58° C.).

(2) Ethyl 4-(2,3-dichlorophenyl)-2-(diethoxycarbonyl)methylamino-4-oxobutyrate The solution of 3.8 g of ethyl 4-(2,3-dichlorophenyl)-2,4-dioxobutyrate, 2.8 g of diethyl aminomalonate hydrochloride and 2.0 g of pyridine in 80 ml of benzene was heated for 8 hours under reflux while removing water produced as a by-product. After cooling the reaction solution, it was washed with aqueous hydrochloric acid and then aqueous sodium carbonate, dehydrated and evaporated to dryness to obtain 1.88 g of ethyl 4-(2,3-dichlorophenyl)-2-(diethoxycarbonyl)methylamino-4-oxo-butyrate.

(3) Dimethyl 3-(2,3-dichlorophenyl)pyrol-2,5-dicarboxylate

To 50 ml of methanol was dissolved 1.88 g of ethyl 4-(2,3-dichlorophenyl)-2-(diethoxycarbonyl)methylamino-4-oxo-butyrate which was produced in the above (2). 0.22 g of anhydrous sodium carbonate was added to the solution and the solution was heated for 4 hours under reflux.

After the reaction, methanol was removed by distillation under reduce pressure and the residue was dissolved in ethyl acetate. The solution was dehydrated and evaporated to dryness under reduced pressure. The residue was recrystallized from methanol to obtain 1 g of dimethyl 3-(2,3-dichlorophenyl)pyrol-2,5-dicarboxylate (m.p. 143°–145° C.).

(4) Dimethyl 4-chloro-3-(2,3-dichlorophenyl)pyrol-2,5-dicarboxylate 0.45 g of sulfuryl chloride was added to the solution of 1 g of dimethyl 3-(2,3-dichlorophenyl)pyrol-2,5-dicarboxylate in 10 ml of acetic acid and it was stirred overnight at room temperature. The reaction solution was evaporated to dryness under reduced pressure and the residue was dissolved in ethyl acetate. After washing the solution with aqueous sodium hydrogencarbonate, it was dehydrated and evaporated to dryness under reduced pressure to obtain 1 g of dimethyl 4-chloro-3-(2,3-dichlorophenyl)propyl-2,5-dicarboxylate (white crystal, m.p. 172°–173° C.).

(5) 4-chloro-3-(2,3-dichlorophenyl)pyrol-2,5-dicarboxylate

The mixture of 1 g of dimethyl 4-chloro-3-(2,3-dichlorophenyl)pyrol-2,5-dicarboxylate, 1 g of sodium hydroxide, 30 ml of ethanol and 18 ml of water was heated for 90 minutes under reflux. After the reaction, ethanol was removed by distillation under reduced pressure and the residue was washed with ether. The aqueous layer was acidified with hydrochloric acid, and then extracted with ethyl acetate. The ethyl acetate layer was washed with water, dehydrated and evaporated to dryness under reduced pressure to obtain 0.93 g of 4-chloro-3-(2,3-dichlorophenyl)pyrol-2,5-dicarboxylic acid (white crystal, d.p. 273° C.).

(6) 4-chloro-3-(2,3-dichlorophenyl)pyrol (Compound No. 1)

The mixture of 53 g of 4-chloro-3-(2,3-dichlorophenyl)pyrol-2,5-dicarboxylic acid, 2.65 g of cupric acid and 80 ml of quinoline was heated at 140°–150° C. for 30 minutes with stirring. To the resulting reaction mixture were added ethyl acetate, ice and concentrated hydrochloric acid which of molar amount was 1.1-time that of employed quinoline. The ethyl acetate layer was washed with successive, water, aqueous sodium carbonate and water. After dehydration, the ethyl acetate layer was evaporated to dryness under reduced pressure to obtain 33.1 g of brown product. The crude product was purified by silicagel chromatography and countercurrent distribution to obtain pale yellow oily substance. The oily substance was recrystallized from n-hexane to obtain 22.5 g of the desired product (colorless or pale yellow needles, m.p. 58°–59° C.).

EXAMPLE 2

Preparation of
1-acetyl-4-chloro-3-(2,3-dichlorophenyl)pyrol
(Compound No. 2)

The mixture of 0.3 g of 4-chloro-3-(2,3-dichlorophenyl)pyrol and 0.6 g of N-acetylimidazole was fused for one hour at 140° C. in a stream of argon. The resulting reaction mixture was purified by thin-layer chromatography to obtain 0.2 g of the desired product (colorless or slightly colored crystal, m.p. 97° C.).

EXAMPLE 3

Preparation of
1-acetyl-4-chloro-3-(3-trifluoromethylphenyl)pyrol
(Compound No. 3)

The mixture of 1 g of 4-chloro-3-(3-trifluoromethylphenyl)pyrol and 2 g of N-acetylimidazole was fused for 1.5 hours at 140°–150° C. The resulding reaction mixture was purified by silicagel chloromatography using 10% solution of aceton in n-hexane as solvent to obtain 0.8 g of the desired product (pale reddish brown crystal, m.p. 70°–71.5° C.).

EXAMPLE 4

Preparation of
1-acetyl-3-(2-chlorophenyl)-4-chloropyrol (Compound No. 4)

The mixture of 4.35 g of 3-(2-chlorophenyl)-4-chloropyrol and 5.3 g of N-acetylimidazole was heated for 4 hours at 100° to 110° C. After cooling, the reaction mixture was dissolved in 200 ml of ether and the resulting ether solution was washed with successive, diluted hydrochloric acid and water. The ether solution was dried with anhydrous sodium sulfate and evaporated to dryness under reduced pressure. The residual crude product was purified by silicagel chromatography using mixed solvent of n-hexane and benzene (1:1) to obtain 2.5 g of the desired product (colorless crystal, m.p. 82°–84° C.).

EXAMPLE 5

Preparation of
1-acetyl-3-(3-chlorophenyl)-4-chloropyrol (Compound No. 5)

The mixture of 6.5 g of 3-(3-chlorophenyl)-4-chloropyrol and 10.1 g of N-acetylimidazole was heated for one hour at 100°–110° C. After cooling, the reaction mixture was dissolved in a mixture of 200 ml of ether and 20 ml of water and the resulting ether solution was treated as in Example 4 to obtain 4.5 g of the desired product (colorless crystal, m.p. 88°–90° C.).

The compounds of the invention possess excellent fungicidal activity when employed to prevent damage to plants, in particular, acetyl compounds, namely the Compound Nos. 2 to 5, possess outstanding residual activity.

The compound may be used directly without mixing with suitable carrier.

The active ingredient of a fungicidal composition exemplifying the invention may be formulated by mixing with suitable carriers in a form generally used in pesticidal compositions, such as wettable powder, emulsifiable concentrate and dust formulation. As solid carriers, bentonite, diatomaceous earth, apatite, gypsum, talc, pyrophyllite, vermiculite and clay, for example, may be used. As liquid carriers, kerosene, mineral oil, petroleum, solvent naphtha, xylene, cyclohexane, cyclohexanone, dimethylformamide, dimethylsulfoxide, alcohol, acetone, benzene and water, for example, may be used. If so desired, a surface active agent may be added in order to give a homogeneous and stable formulation.

The concentration of the active ingredient in the fungicidal composition may vary according to type of formulation, and is for example, 5 to 80 weight percent, preferably 20 to 80 weight percent, in wettable powders; 5 to 70 weight percent, preferably 10 to 50 weight percent, in emulsifiable concentrates; and 0.5 to 20 weight percent, preferably 1 to 10 weight percent, in dust formulation.

Forthermore, the compounds may be used in mixture with other fungicides, insecticides, acaricides and herbicides.

Some non-limiting examples of fungicidal compositions according to the invention are as follows:

EXAMPLE 6

| Wettable Powder | |
|---|---|
| | Parts by weight |
| Compound No. 1 | 20 |
| Diatomaceous earth | 73 |
| Sodium higheralkyl sulfate | 7 |

These are mixed homogeneously and reduced to fine particles to provide a wettable powder containing 20% of the active ingredient.

EXAMPLE 7

| Emulsifiable Concentrate | |
|---|---|
| | parts by weight |
| Compound No. 2 | 20 |
| Xylene | 42 |
| Dimethylformamide | 30 |
| Polyoxyethylene alkylphenyl ether | 8 |

These are mixed and dissolved to provide an emulsifiable concentrate containing 20% of the active ingredient.

| Dust Formulation | |
|---|---|
| | parts by weight |
| Compound No. 3 | 2 |
| Talc | 98 |

These are mixed homogeneously and reduced to fine particles to provide a dust formulation containing 2% of the active ingredient.

The wettable powder or the emulsifiable concentrate is diluted with water to a desired concentration and is used as suspension or emulsion for treating soil, plant or seed. The dust formulation is directly used for treating soil, plant or seed.

The fungicides of the present invention are effective for the control of many plant diseases, for example, by applying to plants, gray mold and Schlerotinia rot of vegetables, leaf mold of tomato, anthracnose, Fusarium wilt and gummy stem blight of cucumber, blast, sheath blight and Helminthosporium leaf spot of rice, stripe of barley, black spot of pear, brown rot of peach, gray mold of grape and scab of apple; by treating soil, anthracnose, Fusarium wilt and gummy stem blight of cucumber; by treating seeds, blast and Helminthosporium leaf spot of rice, bunt of wheat and stripe of barley.

The fungicidal effect of the compounds of this invention is illustrated by the following tests:

Test 1. Test for Control of Gray Mold of Bean

The detached leaves of kidney beans (*Phaseolus vulgaris*) were immersed for about 30 seconds in each aqueous suspension prepared by diluting a wettable powder to different concentrations of a test compound. After air-dried, the treated leaves were inoculated with mycelia of *Botrytis cinerea* and kept at 20° C. in a moist chamber. Control effect was checked 4 days after inoculation. The results are shown in Table 2. Phyto-toxicity was not observed.

TABLE 2

| | Control Value (%) Concentration of Active Ingredient | |
|---|---|---|
| | 12.5 ppm | 6.3 ppm |
| Test Compound No. | | |
| 1 | 100 | 100 |
| 2 | 100 | 100 |
| 3 | 94 | 80 |
| 4 | 100 | 95 |
| 5 | 100 | 100 |
| Comparative Compound* | | |
| 1 | 95 | 70 |
| 2 | 39 | 8 |
| 3 | 75 | 33 |
| 4 | 79 | |
| 5 | 35 | |

*Comparative Compound
1. 4-chloro-3-(2-nitro-3-chlorophenyl)pyrol (Japanese Published Unexamined Patent Application No. 88630/1976)
2. 4-chloro-3-(3,4-dichlorophenyl)pyrol (Japanese Published Examined Patent Application No. 6748/1967)
3. 4-chloro-3-(3-trifluoromethylphenyl)pyrol (Japanese Published Examined Patent Application No. 2011/1975)
4. Rovral (trade name): 1-isopropylcarbamoyl-3-(3,5-dichlorophenyl)hydantoin
5. Euparen (trade name): N'-dichlorofluoromethylthio-N,N-dimethyl-N'-phenylsulfamide Test 2. Test for Control of Gray Mold of Bean (residual effect)

Potted kidney bean (*Phaseolus vulgaris* L.) seedlings, ("Nagauzura", 1.5 leaf stage) were once sprayed with the chemical solution at a concentration of 200 ppm of an active ingredient and then kept in a greenhouse. The leaves were detached and inoculated with mycelium of *Botrytis cinerea* 7 days after spraying and kept in a moist chamber at 20° C. Control effect was checked 4 days after inoculation. The results are shown in Table 3. Pyto-toxicity was not observed.

TABLE 3

| | Control Value (%) |
|---|---|
| Test Compound No. | |
| 2 | 100 |
| 3 | 100 |

TABLE 3-continued

| | Control Value (%) |
|---|---|
| 4 | 100 |
| 5 | 98 |
| Comparative Compound* | |
| 1 | 22 |
| 2 | 10 |
| 3 | 62 |
| 4 | 89 |
| 5 | 64 |

*Comparative Compound: the same as in Test 1.

Test 3. Test for Control of Rhizoctonia Damping-off of Cucumber

Potted cucumber seedlings at the cotyledon stage were treated by injecting an aqueous suspension containing a test compound at 100 ppm into the soil (10 ml/pot) after inoculated with mycelia of *Rhizoctonia solani*. Control effect was evaluated 4 days after inoculation. The results are shown in Table 4. Phyto-toxicity was not observed.

TABLE 4

| | Control Value (%) |
|---|---|
| Test Compound No. | |
| 1 | 100 |
| 2 | 100 |
| 3 | 100 |
| 4 | 100 |
| 5 | 100 |
| Comparative Compound* | |
| 1 | 93 |
| PCNB | 70 |

*Comparative Compound
1.: the same as in Test 1.
PCNB: pentachloronitrobenzene

Test 4. Test for Control of Stripe of Barley by Seed-treatment

Seeds of barley cultivar Kashima were dressed with chemical wettable powder and sown in field one day after seed-dressing. Control effect was evaluated 120 days after seed-sowing. The results are shown in Table 5. Phyto-toxicity was not obserbed.

TABLE 5

| | Control Value (%) Active ingredient (g)/100 kg of seed | | | |
|---|---|---|---|---|
| | 10 | 20 | 30 | 50 |
| Test Compound No. | | | | |
| 1 | 100 | 100 | 100 | |
| 2 | 94 | 98 | 100 | |
| 3 | 97 | 98 | 99 | |
| 4 | 96 | 97 | 100 | |
| 5 | 97 | 93 | 100 | |
| Comparative Compound* | | | | |
| Vitavax | | | | 52 |

*Vitavax: 5,6-dihydro-2-methyl-1,4-oxathiin-3-carboxyanilide

We claim:

1. A fungicidal composition consisting of an inert carrier and a fungicidally effective amount of 4-chloro-3-(2,3-dichlorophenyl)pyrrole.

* * * * *